(12) United States Patent
Kiriki et al.

(10) Patent No.: US 10,633,319 B2
(45) Date of Patent: Apr. 28, 2020

(54) METHOD OF PRODUCING SOLUTION COMPOSITION CONTAINING MONOETHERIFIED PRODUCT, SOLUTION COMPOSITION, AND METHOD OF PRODUCING POLYMERIZABLE COMPOUND

(71) Applicant: ZEON CORPORATION, Chiyoda-ku, Tokyo (JP)

(72) Inventors: Satoshi Kiriki, Tokyo (JP); Kei Sakamoto, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 119 days.

(21) Appl. No.: 16/081,125

(22) PCT Filed: Mar. 1, 2017

(86) PCT No.: PCT/JP2017/008141
§ 371 (c)(1),
(2) Date: Aug. 30, 2018

(87) PCT Pub. No.: WO2017/150622
PCT Pub. Date: Sep. 8, 2017

(65) Prior Publication Data
US 2019/0077738 A1 Mar. 14, 2019

(30) Foreign Application Priority Data
Mar. 1, 2016 (JP) .................................. 2016-038769

(51) Int. Cl.
C07C 43/23 (2006.01)
C07C 41/16 (2006.01)
C07C 67/08 (2006.01)
C07C 41/38 (2006.01)
C07C 41/09 (2006.01)
C08F 2/06 (2006.01)
C08F 22/20 (2006.01)

(52) U.S. Cl.
CPC .............. *C07C 43/23* (2013.01); *C07C 41/09* (2013.01); *C07C 41/16* (2013.01); *C07C 41/38* (2013.01); *C07C 67/08* (2013.01); *C08F 2/06* (2013.01); *C08F 22/20* (2013.01)

(58) Field of Classification Search
CPC ......... C07C 43/23; C07C 41/09; C07C 41/16; C07C 41/38; C07C 67/08; C08F 2/06; C08F 22/20
USPC ...................................................... 526/209
See application file for complete search history.

(56) References Cited

U.S. PATENT DOCUMENTS

| | | | |
|---|---|---|---|
| 4,420,642 A | 12/1983 | Franko-Filipasic et al. | |
| 2004/0209006 A1* | 10/2004 | Matsumoto ........ | C09K 19/3852 428/1.1 |
| 2010/0258764 A1 | 10/2010 | Sakamoto et al. | |

FOREIGN PATENT DOCUMENTS

| | | |
|---|---|---|
| JP | S572230 A | 1/1982 |
| JP | S58144337 A | 8/1983 |
| JP | H06172246 A | 6/1994 |
| JP | 2002037759 A | 2/2002 |
| JP | 2002308831 A | 10/2002 |
| JP | 2015140302 A | 8/2015 |
| WO | 2008133290 A1 | 11/2008 |

OTHER PUBLICATIONS

Bianca M. I. Van Der Zande et al., Mass transport phenomena during lithographic polymerization of nematic monomers monitored with interferometry, Journal of Applied Physics, 2005, pp. 123519-1-123519-8, vol. 97, Issue 12.
Chun-Chieh Huang et al., Synthesis and evaluation of alkoxylated-ether diols of hydroquinone with different chain-lengths as extenders in segmented polyurethanes, J Polym Res, 2015, pp. 1-11, vol. 22, Issue 9.
Jun. 6, 2017, International Search Report issued in the International Patent Application No. PCT/JP2017/008141.
M. J. Whitcombe et al., Synthesis and Photochemistry of Side-Chain Liquid Crystal Polymers Based on Cinnamate Esters, Journal of Polymer Science Part A: Polymer Chemistry, Jul. 1992, pp. 1681-1691, vol. 30, Issue 8.
Sep. 4, 2018, International Preliminary Report on Patentability issued in the International Patent Application No. PCT/JP2017/008141.
Fieser, Louis F. et al., Organic Experiments, Eighth Edition, 5th print, Feb. 10, 2005, pp. 101 to 109, Seishiro Murata.

(Continued)

*Primary Examiner* — William K Cheung
(74) *Attorney, Agent, or Firm* — Kenja IP Law PC

(57) ABSTRACT

Provided is a method of efficiently producing a solution composition containing a monoetherified product (III) using a hydroquinone compound (I) and a hydroxyl group-containing etherifying agent (II). The method of producing a solution composition includes: a step (1) of reacting a hydroquinone compound (I) and a hydroxyl group-containing etherifying agent (II) in a two-phase system including an alkaline aqueous solution and a hydrophobic ether solvent, and in the absence of a phase transfer catalyst and a hydrophilic organic solvent; and a step (2) of separating and removing an aqueous phase of a two-phase reaction liquid by liquid separation, and washing an organic phase using an aqueous solution containing a neutral inorganic salt and a hydroxide of an alkali metal, or the like.

15 Claims, No Drawings

(56) References Cited

OTHER PUBLICATIONS

The Chemical Society of Japan, New Experimental Chemistry Lectures 9 Analytical Chemistry II, May 20, 1977, p. 43, Shingo Iizumi.
Oct. 2, 2019, the Extended European Search Report issued by the European Patent Office in the corresponding European Patent Application No. 17760086.3.

* cited by examiner

METHOD OF PRODUCING SOLUTION COMPOSITION CONTAINING MONOETHERIFIED PRODUCT, SOLUTION COMPOSITION, AND METHOD OF PRODUCING POLYMERIZABLE COMPOUND

This application is a U.S. National Stage Application under 35 U.S.C. § 371 of PCT International Application No. PCT/JP2017/008141 filed Mar. 1, 2017, which claims the priority benefit of Japan Patent Application No. 2016-038769, filed on Mar. 1, 2016, the disclosures of which are incorporated herein in their entirety by reference.

TECHNICAL FIELD

This disclosure relates to a method of producing, with a high yield, a solution composition containing, in high purity, a monoetherified product of a hydroquinone compound that can serve as a production intermediate for a polymerizable compound, a solution composition containing a monoetherified product of a hydroquinone compound, and a method of producing a polymerizable compound using the solution composition.

BACKGROUND

Monoetherified products obtained through monoetherification of hydroquinone compounds are useful, for example, as production intermediates for polymerizable compounds.

Examples of conventional methods for monoetherification of hydroquinone compounds include a method disclosed in NPL 1 and 2 in which a hydroquinone compound and an alkyl halide, or the like, are reacted in the presence of a base in a hydrophilic solvent such as water, an alcohol, acetone, acetonitrile, N,N-dimethylformamide, or dimethyl sulfoxide.

However, there is a problem in terms that when monoetherification of a hydroquinone compound has been attempted using reaction conditions described in NPL 1 and 2, it has not been possible to obtain the target monoetherified product with high yield and high purity.

PTL 1 proposes a method for solving this problem by reacting a dihydroxy compound and a specific etherifying agent in a two-phase system of water and an organic solvent that is substantially water-insoluble to carry out monoetherification of the dihydroxy compound. Moreover, PTL 1 explains that the reaction conversion rate is improved by adding a solvent (cosolvent) that is miscible with both water and the organic solvent to the two-phase system.

However, when a hydroquinone compound and a hydroxyl group-containing etherifying agent are reacted under reaction conditions described in PTL 1, there are cases in which a large amount of a dietherified product of the hydroquinone compound is produced as a by-product and it is difficult to obtain the target monoetherified product in high purity.

The present patent applicant conducted diligent investigation in relation to etherification reactions using hydroquinone compounds and hydroxyl group-containing etherifying agents, and thereby discovered that a monoetherified product can be produced with high yield and high purity by reacting a hydroquinone compound and a hydroxyl group-containing etherifying agent in a two-phase system including an alkaline aqueous solution and a hydrophobic organic solvent (for example, refer to PTL 2).

However, in order to enable even more efficient production of a polymerizable compound, there has been demand for a method by which a monoetherified product that serves as a production intermediate for the polymerizable compound can be obtained with even higher purity and greater efficiency.

CITATION LIST

Patent Literature

PTL 1: JP H6-172246 A
PTL 2: JP 2015-140302 A

Non-Patent Literature

NPL 1: Journal of Polymer Science, Part A: Polymer Chemistry, 30 (8), 1681-1691, 1992
NPL 2: Journal of Applied Physics, 97 (12), 123519/1-123519/8, 2005

SUMMARY

Technical Problem

This disclosure is made in light of the circumstances set forth above and an objective thereof is to provide a method of producing, with better efficiency, higher yield, and higher purity, a solution composition containing a monoetherified product of a hydroquinone compound that is useful as a production intermediate for a polymerizable compound. Another objective of this disclosure is to provide a solution composition containing this monoetherified product and a method of producing a polymerizable compound using the solution composition.

Solution to Problem

As a result of diligent investigation conducted with the aim of solving the problems set forth above, the inventors discovered that a solution composition containing a monoetherified product in high purity can be efficiently obtained by reacting a hydroquinone compound and a hydroxyl group-containing etherifying agent in a two-phase system of an alkaline aqueous solution and a hydrophobic ether solvent, and subsequently washing the resultant organic phase using an aqueous solution containing sodium hydroxide and sodium chloride. The inventors then completed this disclosure through generalization of their findings.

Thus, the following methods [1] to [6] of producing a solution composition, solution compositions [7] and [8], and methods [9] to [11] of producing a polymerizable compound are provided according to this disclosure.

[1] A method of producing a solution composition containing a monoetherified product, comprising:
a step (1) of reacting a hydroquinone compound of formula (I), shown below,

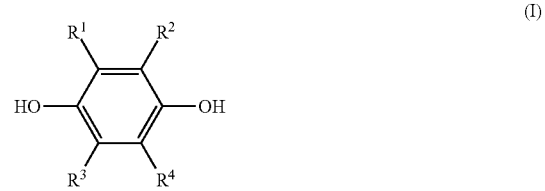

where $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6, and a hydroxyl group-containing etherifying agent of formula (II), shown below,

HO—$R^5$—X    (II)

where $R^5$ represents an optionally substituted alkylene group having a carbon number of 1 to 20 and X represents a leaving group, in a two-phase system including an alkaline aqueous solution and a hydrophobic ether solvent, and in the absence of a phase transfer catalyst and a hydrophilic organic solvent; and a step (2a) of, after the step (1), separating and removing an aqueous phase of a two-phase reaction liquid by liquid separation, and washing an organic phase using an aqueous solution containing a neutral inorganic salt and a hydroxide of an alkali metal or alkaline earth metal or a phosphate of an alkali metal or alkaline earth metal, wherein the monoetherified product is a monoetherified product of formula (III), shown below,

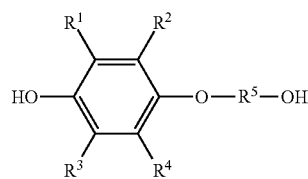

(III)

where $R^1$ to $R^5$ represent the same as above.

[2] The method of producing a solution composition according to [1], wherein
the hydroxide of an alkali metal or alkaline earth metal is sodium hydroxide or potassium hydroxide.

[3] A method of producing a solution composition comprising:
a step (1) of reacting a hydroquinone compound of formula (I), shown below,

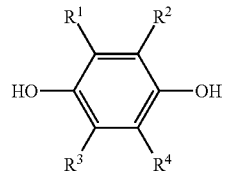

(I)

where $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6, and a hydroxyl group-containing etherifying agent of formula (II), shown below,

HO—$R^5$—X    (II)

where $R^5$ represents an optionally substituted alkylene group having a carbon number of 1 to 20 and X represents a leaving group, in a two-phase system including an alkaline

aqueous solution and a hydrophobic ether solvent, and in the absence of a phase transfer catalyst and a hydrophilic organic solvent; and a step (2b) of, after the step (1), separating and removing an aqueous phase of a two-phase reaction liquid by liquid separation, and washing an organic phase using an aqueous solution containing an alkali and a neutral inorganic salt, wherein the solution composition contains: the hydroquinone compound; a monoetherified product of formula (III), shown below,

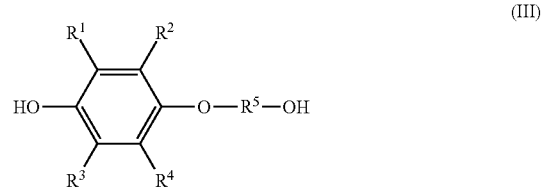

(III)

where $R^1$ to $R^5$ represent the same as above; and a dietherified product of formula (IV), shown below,

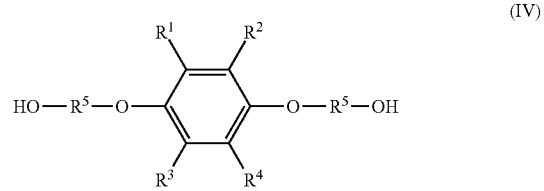

(IV)

where $R^1$ to $R^5$ represent the same as above, and the hydroquinone compound has a molar percentage of 5.0 mol % or less, the monoetherified product has a molar percentage of 85 mol % or more, and the dietherified product has a molar percentage of 10.0 mol % or less relative to the total of the hydroquinone compound, the monoetherified product, and the dietherified product.

[4] The method of producing a solution composition according to any one of [1] to [3], wherein
the hydrophobic ether solvent is anisole or cyclopentyl methyl ether.

[5] The method of producing a solution composition according to any one of [1] to [4], wherein
the neutral inorganic salt is sodium chloride or a sulfate.

[6] The method of producing a solution composition according to any one of [1] to [4], wherein
the neutral inorganic salt is sodium sulfate.

[7] A solution composition comprising:
a hydroquinone compound of formula (I), shown below,

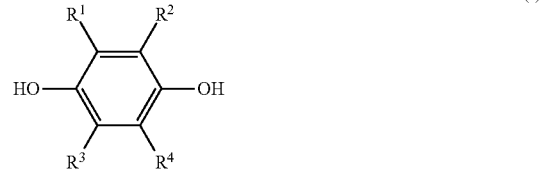

(I)

where $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6;

a monoetherified product of formula (III), shown below,

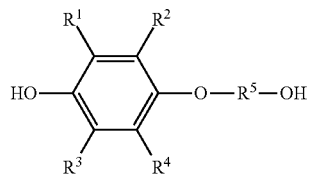

(III)

where $R^1$ to $R^4$ represent the same as above and $R^5$ represents an optionally substituted alkylene group having a carbon number of 1 to 20;

a dietherified product of formula (IV), shown below,

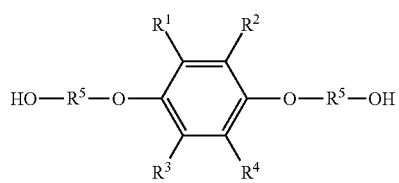

(IV)

where $R^1$ to $R^5$ represent the same as above; and a hydrophobic ether solvent, wherein the hydroquinone compound has a molar percentage of 5.0 mol % or less, the monoetherified product has a molar percentage of 85 mol % or more, and the dietherified product has a molar percentage of 10.0 mol % or less relative to the total of the hydroquinone compound, the monoetherified product, and the dietherified product.

[8] The solution composition according to [7], wherein the hydrophobic ether solvent is anisole or cyclopentyl methyl ether.

[9] A method of producing a polymerizable compound comprising a step (3) of adding an acid catalyst and a carboxylic acid compound of formula (V), shown below,

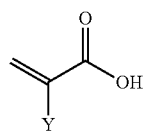

(V)

where Y represents a hydrogen atom, a methyl group, or a chlorine atom, to a solution composition that is obtained by the method according to any one of [1] to [6] or is the solution composition according to [7] or [8], and reacting the carboxylic acid compound with the monoetherified product contained in the solution composition, wherein the polymerizable compound is a polymerizable compound of formula (VI), shown below,

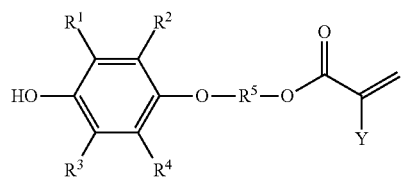

(VI)

where $R^1$ to $R^5$ and Y represent the same as above.

[10] The method of producing a polymerizable compound according to [9], wherein the solution composition is a solution composition obtained by the method according to [6].

[11] The method of producing a polymerizable compound according to [9] or [10], wherein the carboxylic acid compound is acrylic acid.

Advantageous Effect

According to this disclosure, it is possible to efficiently produce a solution composition containing a monoetherified product of a hydroquinone compound in high purity using the hydroquinone compound and a hydroxyl group-containing etherifying agent.

Moreover, a polymerizable compound can be efficiently produced using a presently disclosed solution composition.

Furthermore, a polymerizable compound obtained by a presently disclosed production method is useful as a production intermediate for a polymerizable liquid-crystal compound.

DETAILED DESCRIPTION

The following provides a detailed description of this disclosure split into sections relating to 1) methods (A) and (B) of producing a solution composition containing a monoetherified product, 2) a solution composition, and 3) a method of producing a polymerizable compound.

In the present specification, the phrase "optionally substituted" means "unsubstituted or having one or more substituents".

1) Method (A) of Producing Solution Composition Containing Monoetherified Product A first aspect of this disclosure is a method (A) of producing a solution composition containing a monoetherified product of formula (III), shown below, including the following steps (1) and (2a).

Step (1): A step of reacting a hydroquinone compound of formula (I), shown below, and a hydroxyl group-containing etherifying agent of formula (II), shown below, in a two-phase system including an alkaline aqueous solution and a hydrophobic ether solvent, and in the absence of a phase transfer catalyst and a hydrophilic organic solvent Step (2a): A step of, after step (1), separating and removing an aqueous phase of a two-phase reaction liquid by liquid separation, and washing an organic phase using an aqueous solution containing a neutral inorganic salt and a hydroxide of an alkali metal or alkaline earth metal or a phosphate of an alkali metal or alkaline earth metal <Step (1)>

In this disclosure, step (1) is a step of reacting a hydroquinone compound of formula (I) and a hydroxyl group-containing etherifying agent of formula (II) in a two-phase system including an alkaline aqueous solution and a hydrophobic ether solvent, and in the absence of a phase transfer catalyst and a hydrophilic organic solvent.

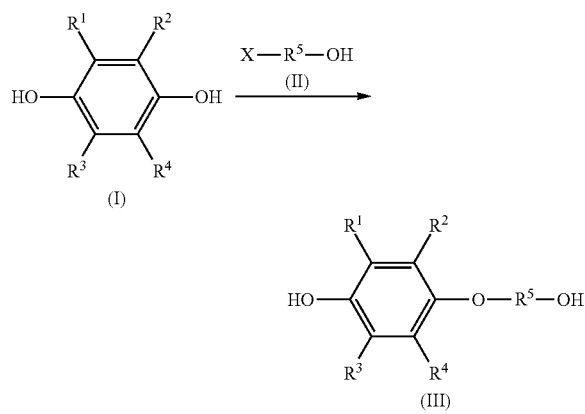

The hydroquinone compound used in this disclosure is a compound of the preceding formula (I) (hereinafter, also referred to as "hydroquinone compound (I)").

In formula (I), $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group. Moreover, R' represents an optionally substituted alkyl group having a carbon number of 1 to 6.

Examples of halogen atoms that may be represented by $R^1$ to $R^4$ include a fluorine atom, a chlorine atom, and a bromine atom.

Examples of the alkyl group having a carbon number of 1 to 6 in the optionally substituted alkyl group having a carbon number of 1 to 6 include a methyl group, an ethyl group, a propyl group, an isopropyl group, an n-butyl group, an isobutyl group, an s-butyl group, a t-butyl group, an n-pentyl group, an isopentyl group, and an n-hexyl group. Examples of possible substituents of such alkyl groups having a carbon number of 1 to 6 include halogen atoms such as a fluorine atom, a chlorine atom, and a bromine atom; alkoxy groups such as a methoxy group and an ethoxy group; a nitro group; and a cyano group.

Note that examples of alkyl groups and substituents thereof for the optionally substituted alkyl group having a carbon number of 1 to 6 of R' include the same alkyl groups having a carbon number of 1 to 6 and substituents thereof as described for $R^1$ to $R^4$.

Of these examples, the used hydroquinone compound (I) is preferably a hydroquinone compound (I) for which $R^1$ to $R^4$ are each, independently of one another, a hydrogen atom or an alkyl group having a carbon number of 1 to 6, and is more preferably a hydroquinone compound (I) for which $R^1$ to $R^4$ are all hydrogen atoms.

The hydroxyl group-containing etherifying agent used in this disclosure is a compound of the previously shown formula (II) (hereinafter, also referred to as "hydroxyl group-containing etherifying agent (II)").

In formula (II), $R^5$ represents an optionally substituted alkylene group having a carbon number of 1 to 20, and X represents a leaving group.

Examples of the alkylene group having a carbon number of 1 to 20 in the optionally substituted alkylene group having a carbon number of 1 to 20 of $R^5$ include a methylene group, an ethylene group, a propylene group, a trimethylene group, a hexamethylene group, an octamethylene group, and a decamethylene group. Examples of possible substituents of such alkylene groups having a carbon number of 1 to 20 include halogen atoms such as a fluorine atom, a chlorine atom, and a bromine atom; alkoxy groups such as a methoxy group and an ethoxy group; a nitro group; and a cyano group.

The leaving group represented by X is not specifically limited and may be a typical leaving group in the field of organic chemistry. Examples include halogen atoms such as a chlorine atom, a bromine atom, and an iodine atom; and an —OSO$_2$R" group (R" represents an optionally substituted alkyl group having a carbon number of 1 to 6 or an optionally substituted aryl group having a carbon number of 6 to 20).

Note that examples of alkyl groups and substituents thereof for the optionally substituted alkyl group having a carbon number of 1 to 6 of R" include the same alkyl groups having a carbon number of 1 to 6 and substituents thereof as described for $R^1$ to $R^4$.

Examples of the aryl group having a carbon number of 6 to 20 in the optionally substituted aryl group having a carbon number of 6 to 20 of R" include a phenyl group, a 1-naphthyl group, and a 2-naphthyl group. Examples of possible substituents of such aryl groups having a carbon number of 6 to 20 include halogen atoms such as a fluorine atom, a chlorine atom, and a bromine atom; alkyl groups having a carbon number of 1 to 6 such as a methyl group and an ethyl group; alkoxy groups such as a methoxy group and an ethoxy group; a nitro group; and a cyano group.

Of these examples, the hydroxyl group-containing etherifying agent (II) in this disclosure is preferably a hydroxyl group-containing etherifying agent (II) for which $R^5$ is an alkylene group having a carbon number of 1 to 10 and X is a halogen atom, and is particularly preferably a hydroxyl group-containing etherifying agent (II) for which $R^5$ is a hexamethylene group and X is a chlorine atom.

In regard to the proportions in which the hydroquinone compound (I) and the hydroxyl group-containing etherifying agent (II) are used, the amount of the hydroquinone compound (I) per 1 mol of the hydroxyl group-containing etherifying agent (II) is preferably 1.0 mol or more, and more preferably 1.1 mol or more, and is preferably 2.0 mol or less, and more preferably 1.5 mol or less.

If the proportion in which the hydroquinone compound (I) is used is too small, a larger amount of dietherified product tends to be produced, and the yield and purity of the monoetherified product tend to decrease. On the other hand, if the proportion in which the hydroquinone compound (I) is used is too large, it may become difficult to sufficiently reduce the amount of the hydroquinone compound (I) that is present in the resultant solution composition.

The reaction of the hydroquinone compound (I) and the hydroxyl group-containing etherifying agent (II) in step (1) (monoetherification reaction of hydroquinone compound (I)) is carried out in a two-phase system of an alkaline aqueous solution and a hydrophobic ether solvent.

By carrying out the reaction in a two-phase system, further etherification reaction of the monoetherified product can be inhibited, and the amount of dietherified product that is produced can be reduced. Moreover, through use of the alkaline aqueous solution, acid produced in accompaniment to progression of the reaction can be neutralized to enable more efficient monoetherification of the hydroquinone compound (I).

The alkaline aqueous solution may be obtained by dissolving an inorganic base such as a metal carbonate, a metal hydrogen carbonate, or a metal hydroxide in water. The water that is used is preferably distilled water or the like that does not contain impurities.

Examples of metal carbonates that may be used include alkali metal carbonates such as sodium carbonate and potassium carbonate; magnesium carbonate; and alkaline earth metal carbonates such as calcium carbonate and barium carbonate.

Examples of metal hydrogen carbonates that may be used include alkali metal hydrogen carbonates such as sodium hydrogen carbonate and potassium hydrogen carbonate; magnesium hydrogen carbonate; and alkaline earth metal hydrogen carbonates such as calcium hydrogen carbonate.

Examples of metal hydroxides that may be used include alkali metal hydroxides such as sodium hydroxide and potassium hydroxide; magnesium hydroxide; and alkaline earth metal hydroxides such as calcium hydroxide.

One of these inorganic bases may be used individually, or two or more of these inorganic bases may be used in combination.

Of these inorganic bases, a metal hydroxide is preferable, and sodium hydroxide or potassium hydroxide is more preferable since this enables the monoetherified product to be obtained with a good yield.

The content of the inorganic base in the alkaline aqueous solution per 1 mol of the hydroxyl group-containing etherifying agent (II) is preferably 1.00 mol or more, and more preferably 1.05 mol or more, and is preferably 2.00 mol or less, and more preferably 1.30 mol or less.

If the content of the inorganic base is too low, the yield of the monoetherified product may decrease, the rate of reaction may slow, and a large amount of the hydroxyl group-containing etherifying agent (II) may remain unreacted. On the other hand, if the content of the inorganic base is too high, a separate post-reaction neutralization step becomes necessary.

No specific limitations are placed on the amount of the alkaline aqueous solution that is used other than being an amount that enables dissolution of the hydroquinone compound (I).

The amount of the alkaline aqueous solution that is used per 1 part by mass of the hydroxyl group-containing etherifying agent (II) is preferably 2 parts by mass or more, and more preferably 3 parts by mass or more, and is preferably 10 parts by mass or less, and more preferably 5 parts by mass or less.

If too much of the alkaline aqueous solution is used, the rate of reaction may slow, and productivity may fall. On the other hand, if too little of the alkaline aqueous solution is used, precipitation of a raw material compound or the like may occur, viscosity of the solution may increase, and the rate of reaction may decrease.

The hydrophobic ether solvent used in this disclosure is an ether solvent for which solubility in 100 g of water at 25° C. is 10 g/100 g-$H_2O$ or less.

The hydrophobic ether solvent is a solvent in which solubility of the target monoetherified product (III) is high. Accordingly, as a result of the hydrophobic ether solvent being used, separation occurs into two phases in the form of an aqueous phase containing a large amount of unreacted raw material hydroquinone compound (I) and an organic phase containing a large amount of the target once the reaction has ended, rather than into three phases in the form of solvent, target, and water, and consequently a liquid separation operation can be easily carried out. This can increase the molar percentage of the monoetherified product (III) in the resultant solution composition.

Examples of hydrophobic ether solvents that may be used include aryl ether solvents such as anisole, phenetole, butyl phenyl ether, pentyl phenyl ether, diphenyl ether, cresyl methyl ether, and 1,2-dimethoxybenzene; cycloalkyl ether solvents such as cyclopentyl methyl ether (CPME) and cyclohexyl methyl ether; alkyl ether solvents such as diethyl ether, ethyl isoamyl ether, ethyl t-butyl ether, ethyl benzyl ether, diisoamyl ether, dipropyl ether, diisopropyl ether, dibutyl ether, dihexyl ether, dibenzyl ether, and methyl t-butyl ether; and glycol ether solvents such as 1,2-diethoxyethane, 1,2-dibutoxyethane, and diethylene glycol dibutyl ether.

Of these hydrophobic ether solvents, a hydrophobic ether solvent that does not form an azeotrope with water or has an azeotropic boiling point with water of 80° C. or higher is preferable because this allows the reaction to be carried out under high temperature in a short time. Moreover, an aryl ether solvent or a cycloalkyl ether solvent is more preferable, and anisole or cyclopentyl methyl ether is particularly preferable for reasons such as facilitating selective acquisition of the monoetherified product (III) and being superior from a financial perspective.

The amount of the hydrophobic ether solvent that is used per 1 part by mass of the hydroxyl group-containing etherifying agent (II) is preferably 0.2 parts by mass or more, and more preferably 0.5 parts by mass or more, and is preferably 10 parts by mass or less, and more preferably 2 parts by mass or less.

If too much of the hydrophobic ether solvent is used, the rate of reaction may slow, and productivity may fall. On the other hand, if too little of the hydrophobic ether solvent is used, it becomes difficult to achieve the effect brought about by using the hydrophobic ether solvent, and selective synthesis of the monoetherified product may become difficult.

In this disclosure, the reaction of the hydroquinone compound (I) and the hydroxyl group-containing etherifying agent (II) is carried out in the absence of a phase transfer catalyst and a hydrophilic organic solvent.

Herein, "in the absence of a phase transfer catalyst and a hydrophilic organic solvent" means that a phase transfer catalyst and a hydrophilic organic solvent are not substantially present in the reaction system. Specifically, this refers to a case in which, for example, the total amount of phase transfer catalyst and hydrophilic organic solvent relative to the total of the alkaline aqueous solution and the hydrophobic ether solvent is 0.01 mass % or less, and preferably 0.001 mass % or less.

By carrying out the reaction "in the absence of a phase transfer catalyst and a hydrophilic organic solvent", the reaction can be more efficiently carried out in a two-phase system, and the monoetherified product (III) can be selectively synthesized.

Examples of phase transfer catalysts include catalysts that are commonly known in the field of organic synthetic chemistry. Specific examples include, but are not limited to, quaternary ammonium halides such as tetramethylammonium bromide, tetramethylammonium chloride, tetraethylammonium bromide, tetrapropylammonium bromide, tetrabutylammonium bromide, tetrabutylammonium chloride, cetyltrimethylammonium bromide, benzyltriethylammonium chloride, and trioctylmethylammonium chloride; quaternary phosphonium halides such as tetrabutylphosphonium bromide, benzyltriphenylphosphonium bromide, and butyltriphenylphosphonium bromide; crown ethers such as 15-crown-5, 18-crown-6, dibenzo-18-crown-6, dibenzo-24-crown-8, and dicyclohexyl-18-crown-6; and polyoxyalkylene glycols such as polyethylene glycol, polypropylene glycol, and polyethylene glycol monomethyl ether.

The term "hydrophilic organic solvent" refers to an organic solvent for which solubility in 100 g of water at 25° C. is more than 10 g/100 g-$H_2O$.

Examples of hydrophilic organic solvents include alcohol solvents such as methanol, ethanol, isopropanol, ethylene glycol, and methyl cellosolve; hydrophilic ether solvents such as tetrahydrofuran and dioxane; and ketone solvents such as acetone.

The hydroquinone compound (I) is highly susceptible to oxidation under alkaline conditions. Accordingly, the reaction of the hydroquinone compound (I) and the hydroxyl group-containing etherifying agent (II) is preferably carried out in an inert gas atmosphere of nitrogen gas, argon gas, or the like.

Moreover, a reducing agent is preferably added to the reaction liquid in order to inhibit oxidation of the hydroquinone compound (I).

Examples of reducing agents that may be used include sodium sulfite (anhydrous), sodium sulfite heptahydrate, sodium thiosulfate (anhydrous), and sodium thiosulfate pentahydrate.

The amount of the reducing agent that is used per 1 part by mass of the hydroquinone compound (I) is preferably 0.01 parts by mass or more, and more preferably 0.02 parts by mass or more, and is preferably 0.2 parts by mass or less, and more preferably 0.1 parts by mass or less.

Through addition of the reducing agent, coloring of the reaction liquid due to oxidation can be significantly suppressed even without removal of air in the reaction vessel or dissolved in solvent.

The specific method by which the reaction of the hydroquinone compound (I) and the hydroxyl group-containing etherifying agent (II) is carried out may be as follows.

First, specific amounts of the hydroquinone compound (I), the hydroxyl group-containing etherifying agent (II), the alkaline aqueous solution, the hydrophobic ether solvent, and the reducing agent, as desired, are added into a specific reaction vessel in an inert atmosphere. No specific limitations are placed on the order in which these materials are added. The alkaline aqueous solution may be added into the reaction vessel as a pre-prepared alkaline aqueous solution or may be prepared in the reaction vessel by separately adding distilled water and an inorganic base into the reaction vessel.

Moreover, the entire amount of the inorganic base (or alkaline aqueous solution) and the hydroxyl group-containing etherifying agent (II) may be initially added into the reaction vessel, or the inorganic base (or alkaline aqueous solution) and the hydroxyl group-containing etherifying agent (II) may be gradually added into the reaction vessel over multiple additions.

Although no specific limitations are placed on the reaction temperature, the reaction temperature is normally at least 20° C. and not higher than 200° C., is preferably 60° C. or higher, and more preferably 80° C. or higher, and is preferably 150° C. or lower, and more preferably 120° C. or lower. In a situation in which the reaction is slow even when the reaction temperature is increased to the boiling point, the reaction may be carried out under pressurized conditions using an autoclave or the like so that the reaction can be carried out at a higher reaction temperature.

The reaction time is normally at least 1 hour and not more than 24 hours but is dependent on the reaction temperature and so forth.

Progress of the reaction can be checked by commonly known analytical means (for example, thin-layer chromatography, high-performance liquid chromatography, or gas chromatography).

<Step (2a)>

Step (2a) is a step of, after step (1), separating and removing an aqueous phase of the resultant two-phase reaction liquid by liquid separation, and washing an organic phase using an aqueous solution containing a neutral inorganic salt and a hydroxide of an alkali metal or alkaline earth metal or a phosphate of an alkali metal or alkaline earth metal (hereinafter, these hydroxides and phosphates may also be referred to collectively as "alkali metal hydroxides and the like"). This solution is also referred to below simply as the "washing aqueous solution".

Examples of alkali metal hydroxides and the like that may be used in preparation of the washing aqueous solution include hydroxides of alkali metals such as sodium hydroxide and potassium hydroxide; hydroxides of alkaline earth metals such as calcium hydroxide; phosphates of alkali metals such as trisodium phosphate and tripotassium phosphate; and phosphates of alkaline earth metals such as calcium phosphate.

Of these alkali metal hydroxides and the like, a hydroxide of an alkali metal or a phosphate of an alkali metal is preferable, sodium hydroxide, potassium hydroxide, or tripotassium phosphate is more preferable, and sodium hydroxide or potassium hydroxide is even more preferable.

Although no specific limitations are placed on the amount of the alkali metal hydroxide or the like that is used, the amount relative to the number of moles of the hydroquinone compound (I) used in excess relative to the hydroxyl group-containing etherifying agent (II) (i.e., the number of moles calculated by subtracting the number of moles of the hydroxyl group-containing etherifying agent (II) that are used from the number of moles of the hydroquinone compound (I) that are used) is preferably 0.2 molar equivalents or more, and more preferably 0.4 molar equivalent or more, and is preferably 1.0 molar equivalents or less, and more preferably 0.8 molar equivalents or less.

The neutral inorganic salt is an inorganic salt that yields a roughly neutral aqueous solution when dissolved in water. The neutral inorganic salt used in this disclosure is preferably readily soluble in water, and is more preferably an inorganic salt that, for example, dissolves in 1,000 g of water at 25° C. in an amount of 50 g or more. Specifically, the neutral inorganic salt may be an inorganic salt that yields an aqueous solution having a pH at least 5.0 and not higher than 8.0 when 50 g of the inorganic salt is dissolved in 1 L of water at 25° C.

Moreover, the neutral inorganic salt may be anhydrous, or may be a hydrate such as sodium sulfate pentahydrate.

Specific examples of neutral inorganic salts that may be used include alkali metal halides such as sodium chloride, potassium chloride, sodium bromide, and potassium bromide; magnesium halides such as magnesium chloride and magnesium bromide; alkaline earth metal halides such as calcium chloride; alkali metal sulfates such as sodium sulfate; magnesium sulfate; alkali metal nitrates such as sodium nitrate and potassium nitrate; and alkali metal borates such as sodium borate and potassium borate.

One of these neutral inorganic salts may be used individually, or two or more of these neutral inorganic salts may be used in combination.

Of these neutral inorganic salts, an alkali metal halide or a sulfate is preferable, sodium chloride or a sulfate is more preferable, sodium chloride or an alkali metal sulfate is even more preferable, and sodium chloride or sodium sulfate is particularly preferable from a viewpoint of ease of acquisition and solubility in water.

The sodium chloride is not specifically limited and may be industrial salt, namishio, common salt, rock salt, sea salt, natural salt, salt pan salt, or the like. The purity of the sodium chloride is normally 93 mass % or more, and preferably 95 mass % or more.

In a case in which an alkali metal halide such as sodium chloride is used, this may lead to generation of hydrogen halide and by-product production in a subsequently described step of producing a polymerizable compound. Therefore, the use of a sulfate that does not contain a halogen is preferable from a viewpoint of obtaining a solution composition containing a higher-purity polymerizable compound (VI).

Specifically, when a solution composition obtained by the presently disclosed production method (A) is used in production of a solution composition containing a polymerizable compound (IV), it is possible to obtain a solution composition that contains a high-purity polymerizable compound (VI) and in which the content of a compound of the following formula (VII) (hereinafter, also referred to as "compound (VII)") is 0.1 mass % or less in a situation in which the washing in step (2a) has been performed using a neutral inorganic salt that does not include a halogen.

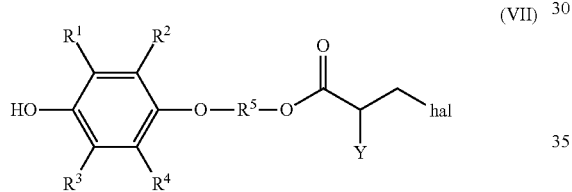

(In formula (VII), $R^1$ to $R^5$ and Y represent the same as above, and "hal" represents a halogen atom.)

Although no specific limitations are placed on the amount of the neutral inorganic salt that is used, the amount in 1 part by mass of the washing aqueous solution is normally at least 0.03 parts by mass and not more than 0.5 parts by mass, and preferably at least 0.1 parts by mass and not more than 0.3 parts by mass.

When the amount of the neutral inorganic salt that is used is within any of the ranges set forth above, hydroquinone compound (I) remaining in the organic phase can be caused to move into the aqueous phase more selectively, which facilitates removal of the hydroquinone compound (I) through the liquid separation operation.

The amount of the washing aqueous solution that is used per 1 part by mass of the hydroxyl group-containing etherifying agent (II) used in step (1) is preferably 2 parts by mass or more, and more preferably 3 parts by mass or more, and is preferably 10 parts by mass or less, and more preferably 7 parts by mass or less.

In step (2a) in which the organic phase is washed using the washing aqueous solution, a reducing agent may be added in order to inhibit oxidation due to air in the same way as in step (1). Examples of reducing agents that may be used include the same reducing agents given as examples for step (1).

The amount of the reducing agent that is used in step (2a) per 1 part by mass of the hydroquinone compound (I) used in step (1) is preferably 0.01 parts by mass or more, and more preferably 0.02 parts by mass or more, and is preferably 0.2 parts by mass or less, and more preferably 0.1 parts by mass or less.

No specific limitations are placed on the method by which the organic phase obtained through liquid separation of the two-phase reaction liquid obtained in step (1) is washed using the washing aqueous solution.

For example, the washing may be carried out by adding the washing aqueous solution and the reducing agent, as desired, to the organic phase, stirring the entire contents for a few minutes to several hours, and preferably 10 minutes to 2 hours, at a temperature of at least 0° C. and not higher than 80° C., and preferably at least 50° C. and not higher than 70° C., leaving the entire contents at rest for approximately 1 minute to 60 minutes, and subsequently removing the phase-separated aqueous phase.

The resultant organic phase is a solution composition that contains a monoetherified product represented by the previously shown formula (III) (hereinafter, also referred to as "monoetherified product (III)").

Besides the monoetherified product (III), the resultant solution composition normally contains the hydroquinone compound (I) as an unreacted raw material and a dietherified product of the following formula (IV) (hereinafter, also referred to as "dietherified product (IV)").

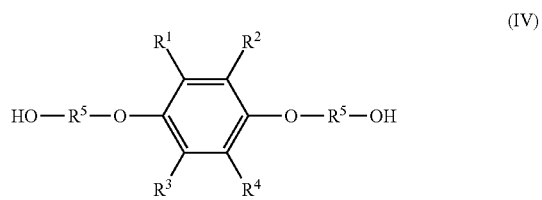

(In formula (IV), $R^1$ to $R^5$ represent the same as above.)

Relative to the total of the hydroquinone compound (I), the monoetherified product (III), and the dietherified product (IV) in the resultant solution composition, the molar percentage of the hydroquinone compound (I) is preferably 5.0 mol % or less, and more preferably 4.0 mol % or less, the molar percentage of the monoetherified product (III) is preferably 85 mol % or more, and more preferably 87.0 mol % or more, and the molar percentage of the dietherified product (IV) is preferably 10.0 mol % or less, and more preferably 9.5 mol % or less.

2) Method (B) of Producing Solution Composition Containing Monoetherified Product A second aspect of this disclosure is a method (B) of producing a solution composition including the following steps (1) and (2b). A solution composition obtained by the production method (B) contains a hydroquinone compound (I), a monoetherified product (III), and a dietherified product (IV), wherein the hydroquinone compound (I) has a molar percentage of 5.0 mol % or less, the monoetherified product (III) has a molar percentage of 85 mol % or more, and the dietherified product (IV) has a molar percentage of 10.0 mol % or less relative to the total of the hydroquinone compound (I), the monoetherified product (III), and the dietherified product (IV).

Step (1): A step of reacting the hydroquinone compound (I) and the hydroxyl group-containing etherifying agent (II) in a two-phase system including an alkaline aqueous solution and a hydrophobic ether solvent, and in the absence of a phase transfer catalyst and a hydrophilic organic solvent Step (2b): A step of, after step (1), separating and removing an aqueous phase of a two-phase reaction liquid by liquid separation, and washing an organic phase using an aqueous solution containing an alkali and a neutral inorganic salt <Step (1)>

Step (1) may be carried out in the same manner as described in relation to the production method (A).

<Step (2b)>

Step (2b) is a step of, after step (1), separating and removing an aqueous phase of the resultant two-phase reaction liquid by liquid separation, and washing an organic phase using an aqueous solution containing an alkali and a neutral inorganic salt.

In this manner, it is possible to obtain a solution composition that contains the hydroquinone compound (I), the monoetherified product (III), and the dietherified product (IV), and in which the hydroquinone compound (I) has a molar percentage of 5.0 mol % or less, and preferably 4.0 mol % or less, the monoetherified product (III) has a molar percentage of 85 mol % or more, and preferably 87.0 mol % or more, and the dietherified product (IV) has a molar percentage of 10.0 mol % or less, and preferably 9.5 mol % or less.

No specific limitations are placed on the alkali used in the aqueous solution for washing the organic phase in step (2b). Among alkalis, a metal hydroxide that has high solubility in water and exhibits strong alkalinity is preferable, a hydroxide of an alkali metal is more preferable, and sodium hydroxide or potassium hydroxide is even more preferable. By using an alkali such as described above, a solution composition having the previously described make-up can be efficiently produced.

Although no specific limitations are placed on the amount of the alkali that is used, the amount relative to the number of moles of the hydroquinone compound (I) used in excess relative to the hydroxyl group-containing etherifying agent (II) (i.e., the number of moles calculated by subtracting the number of moles of the hydroxyl group-containing etherifying agent (II) that are used from the number of moles of the hydroquinone compound (I) that are used) is preferably 0.2 molar equivalents or more, and more preferably 0.4 molar equivalent or more, and is preferably 1.0 molar equivalents or less, more preferably 0.9 molar equivalents or less, and even more preferably 0.8 molar equivalents or less.

The neutral inorganic salt used in the aqueous solution for washing the organic phase may be any of the neutral inorganic salts described in relation to the production method (A), and is preferably sodium chloride or a sulfate, more preferably sodium chloride or an alkali metal sulfate, and even more preferably sodium chloride or sodium sulfate. By carrying out washing using an alkali metal sulfate in step (2b), it is possible to obtain a high-purity polymerizable compound (VI) with content of a by-product compound of the previously shown formula (VII) among the resultant reaction product of 0.1 mass % or less.

Although no specific limitations are placed on the amount of the neutral inorganic salt that is used, the amount in 1 part by mass of the aqueous solution for washing the organic phase is normally at least 0.03 parts by mass and not more than 0.5 parts by mass, and preferably at least 0.1 parts by mass and not more than 0.3 parts by mass.

The presently disclosed production method (B) enables efficient acquisition of a solution composition containing a high-purity monoetherified product.

The monoetherified product (III) contained in the solution composition obtained by the presently disclosed production method (B) is useful as a production intermediate for a polymerizable liquid-crystal compound. For example, an high-purity polymerizable compound can be obtained by using the obtained solution composition to react the monoetherified product (III) and a carboxylic acid compound of formula (V) as subsequently described. This polymerizable compound can then be used to efficiently produce a high-purity polymerizable liquid-crystal compound.

3) Solution Composition

A third aspect of this disclosure is a solution composition containing a hydroquinone compound (I), a monoetherified product (III), a dietherified product (IV), and a hydrophobic ether solvent, wherein the hydroquinone compound (I) has a molar percentage of more than 0 mol % and not more than 5.0 mol %, and preferably more than 0 mol % and not more than 4.0 mol %, the monoetherified product (III) has a molar percentage of at least 85.0 mol % and less than 100.0 mol %, and preferably at least 87.0 mol % and less than 100.0 mol %, and the dietherified product (IV) has a molar percentage of more than 0 mol % and not more than 10.0 mol %, and preferably more than 0 mol % and not more than 9.5 mol % relative to the total of the hydroquinone compound (I), the monoetherified product (III), and the dietherified product (IV).

The hydrophobic ether solvent may be any of the hydrophobic ether solvents given as examples in relation to the presently disclosed methods of producing a solution composition.

The presently disclosed solution composition is preferably produced using the presently disclosed method (A) or (B) of producing a solution composition set forth above.

The presently disclosed solution composition is useful as a production raw material for a subsequently described polymerizable compound.

4) Method of Producing Polymerizable Compound

A fourth aspect of this disclosure is a method of producing a polymerizable compound of the following formula (VI) (hereinafter, also referred to as "polymerizable compound (VI)") including a step (3) of adding an acid catalyst and a carboxylic acid compound of formula (V) (hereinafter, also referred to as "carboxylic acid compound (V)") to a solution composition obtained by a presently disclosed method of producing a solution composition, and reacting the carboxylic acid compound (V) with the monoetherified product (III) contained in the solution composition.

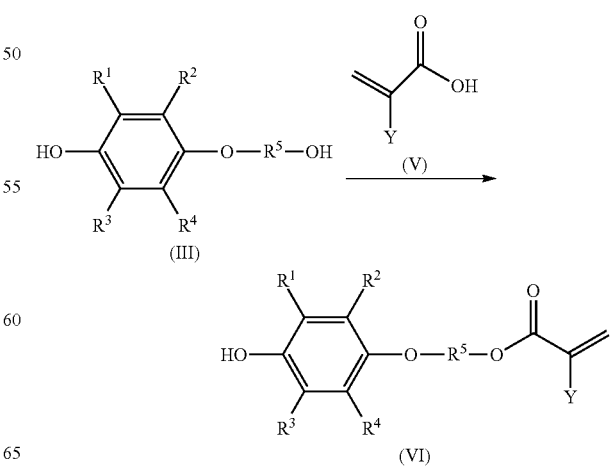

In the preceding formulae, $R^1$ to $R^5$ represent the same as above. Y represents a hydrogen atom, a methyl group, or a chlorine atom, and is preferably a hydrogen atom.

Step (3) is a step of obtaining the polymerizable compound (VI) through a dehydration condensation reaction of the monoetherified product (III), which includes an alcoholic hydroxy group, and the carboxylic acid compound (V), which includes a carboxyl group.

In this disclosure, it is preferable to use a solution composition that is obtained through washing using a sulfate, preferably an alkali metal sulfate, and more preferably sodium sulfate as the neutral inorganic salt in the previously described step (2). (Note that "step (2)" refers to step (2a) of production method (A) or step (2b) of production method (B); the same applies below.) This is because production of the previously described compound (VII) can be inhibited, and a higher purity polymerizable compound (VI) can be obtained by carrying out washing using a neutral inorganic salt that does not include a halogen such as chlorine and, as a result, a solution composition containing a high-purity polymerizable compound (VI) can be obtained.

The proportions in which the solution composition and the carboxylic acid compound (V) are used are preferably amounts such that the molar ratio of the monoether compound (III) in the solution composition and the carboxylic acid compound (V) (monoether compound (III):carboxylic acid compound (V)) is 1:1 to 1:10, and more preferably 1:2 to 1:4.

Examples of acid catalysts that may be used include, but are not specifically limited to, mineral acids such as hydrochloric acid, sulfuric acid, phosphoric acid, and nitric acid; heteropoly acids such as phosphotungstic acid; organic acids such as methanesulfonic acid and p-toluenesulfonic acid; sulfonic acid-type strongly acidic ion exchange resins such as Amberlyst® (Amberlyst is a registered trademark in Japan, other countries, or both), Amberlite® (Amberlite is a registered trademark in Japan, other countries, or both), and DOWEX® (DOWEX is a registered trademark in Japan, other countries, or both); sulfonic acid-type fluorinated alkylene resins such as sulfonated tetrafluoroethylene resin; inorganic solid acids such as mordenite and zeolite; and other conventional and commonly known acid catalysts.

Although no specific limitations are placed on the amount of the acid catalyst that is used, the amount per 1 mol of the monoetherified product (III) is normally at least 0.05 mol and not more than 0.6 mol, and preferably at least 0.1 mol and not more than 0.4 mol.

The dehydration condensation reaction can be carried through addition of only the carboxylic acid compound (V) and the acid catalyst to the solution composition, but may be carried out with further addition of a solvent.

Examples of solvents that may be used include amide solvents such as N-methylpyrrolidone, N,N-dimethylformamide, and N,N-dimethylacetamide; ether solvents such as tetrahydrofuran, 1,3-dimethoxyethane, and 1,4-dioxane; sulfur-containing solvents such as dimethyl sulfoxide and sulfolane; aliphatic hydrocarbon solvents such as n-pentane and n-hexane; alicyclic hydrocarbon solvents such as cyclopentane and cyclohexane; aromatic hydrocarbon solvents such as benzene, toluene, and xylene; and mixed solvents of two or more of these solvents.

Of these solvents, an aromatic hydrocarbon solvent is preferable, and toluene is more preferable.

Although no specific limitations are placed on the amount of the solvent that is used, the amount per 1 part by mass of the hydrophobic ether solvent is preferably 0.2 parts by mass or more, and more preferably 0.5 parts by mass or more, and is preferably 10 parts by mass or less, and more preferably 2 parts by mass or less.

It is preferable that the dehydration condensation reaction is carried out while removing produced water from the system from a viewpoint of obtaining the target with a good yield. The method by which the reaction is carried out while removing produced water from the system may, for example, be a method in which the reaction is carried out while removing water from the system using a water removal apparatus such as a Dean-Stark apparatus; a method in which the reaction is carried out while providing a dehydrating agent such as a molecular sieve in the reaction system to remove water produced in the reaction; a method of carrying out the reaction while removing water from the system as an azeotrope with benzene or the like; or a method in which the reaction is carried out while chemically capturing water produced in the system using an orthoester, N,N-dicyclohexylcarbodiimide, or the like.

Moreover, it is preferable that water is removed in advance even before initiating the dehydration condensation reaction from a viewpoint of more efficiently obtaining the target.

The dehydration condensation reaction may be carried in the presence of a polymerization inhibitor in order to stabilize the carboxylic acid compound (V) and the polymerizable compound (VI) (i.e., prevent polymerization). Examples of polymerization inhibitors that may be used include 2,6-di(t-butyl)-4-methylphenol (BHT), 2,2'-methylenebis(6-t-butyl-p-cresol), triphenyl phosphite, and tris(nonylphenyl) phosphite.

In a case in which a polymerization inhibitor is used, the amount thereof per 100 parts by mass of the monoetherified product (III) is normally at least 0.1 parts by mass and not more than 10 parts by mass, and preferably at least 0.5 parts by mass and not more than 5 parts by mass.

Although no specific limitations are placed on the reaction temperature of the dehydration condensation reaction, the reaction temperature is normally at least 0° C. and not higher than 150° C., preferably at least 20° C. and not higher than 120° C., and more preferably at least 40° C. and not higher than 80° C.

In a case in which the dehydration condensation reaction is carried out while removing water from the system azeotropically, the reaction is preferably carried out while increasing or reducing pressure in the reaction vessel such that azeotropic boiling occurs at the desired reaction temperature.

The reaction time is normally at least 1 hour and not more than 24 hours but is dependent on the reaction temperature and so forth.

Progress of the reaction can be checked by commonly known analytical means (for example, thin-layer chromatography, high-performance liquid chromatography, or gas chromatography).

After the reaction has ended, an after-treatment operation that is typically used in organic synthetic chemistry may be carried out and the reaction product may be purified as desired by a commonly known separation/purification means such as distillation, column chromatography, or recrystallization to thereby efficiently isolate the target polymerizable compound (VI). For example, the target polymerizable compound (VI) may be isolated by neutralizing the post-reaction solution through addition of an alkaline aqueous solution, removing the aqueous phase, washing the organic phase with water, and subsequently precipitating crystals through addition of a poor solvent to the organic phase.

The structure of the target can be identified and confirmed by analytical means such as an NMR spectrum, an IR spectrum, or a mass spectrum.

In this disclosure, in a case in which the polymerizable compound (VI) is isolated by recrystallization or reprecipitation, it is typically preferable that a hydrocarbon solvent such as hexane or toluene is used as the poor solvent. In such a situation, it is preferable to add an antistatic agent for safety improvement because there is a risk of static electricity ignition occurring in a step of filtering crystals.

The antistatic agent that is used is required to dissolve in a hydrocarbon solvent and may, for example, be an antistatic agent for fuel oil. Specific examples of antistatic agents that may be used include STADIS-450 and STADIS-425 produced by Innospec Inc.

The amount of the antistatic agent that is used is normally at least 10 ppm and not more than 5,000 ppm relative to the total weight of solvent. The conductivity of the solvent is preferably $10^{-9}$ S/m or more, which is regarded as a safe guideline.

The polymerizable compound (VI) obtained according to this disclosure is useful as a production intermediate for a polymerizable liquid-crystal compound (for example, refer to WO 2008/133290 A1). The presently disclosed method of producing a polymerizable compound enables simple and efficient synthesis of a high-purity polymerizable compound (VI) because a solution composition in which content of the hydroquinone compound (I) and the dietherified product (IV) is low and content of the monoetherified product (III) is high can be used in this form as a starting material.

EXAMPLES

The following provides a more detailed description of this disclosure through examples. However, this disclosure is not in any way limited by the following examples.

In the following examples and comparative examples, the make-up of solution compositions was analyzed by high-performance liquid chromatography.

In this analysis, the molar percentages of hydroquinone compound (I), monoetherified product (III), and dietherified product (IV) were each calculated by preparing a calibration curve using a high-purity reference substance.

Moreover, the purity of 6-[(4-hydroxyphenyl)oxy]hexyl acrylate in the following examples was determined from peak area proportions according to high-performance liquid chromatography analysis.

<High-performance Liquid Chromatography Measurement Conditions>

The measurement conditions in high-performance liquid chromatography were as follows.

Apparatus: 1200 Series produced by Agilent

Eluent: Mixed liquid of acetonitrile (liquid A) and 0.1% trifluoroacetic acid aqueous solution (liquid B)

Retention conditions: Volume ratio of liquid A and liquid B (liquid A:liquid B) retained at 50:50 for 3 minutes, subsequently changed continuously from 50:50 to 95:5 over 7 minutes, and then retained at 95:5 for 10 minutes Column: ZORBAX Bonus-RP (4.6 mm in diameter×250 mm in length) (880668-901 produced by Agilent)
Temperature: 40° C.
Flow rate: 1 mL/min
Detection UV wavelength: 280 nm Synthesis Example 1 Liquid Make-up Analysis of Organic Phase After Step (1)

A three-necked reaction vessel equipped with a condenser and a thermometer was charged with 104.77 g (0.9515 mol) of hydroquinone, 100 g (0.7320 mol) of 6-chlorohexanol, 500 g of distilled water, and 100 g of anisole in a stream of nitrogen. The entire contents of the reaction vessel were stirred while further adding 35.13 g (0.8784 mol) of sodium hydroxide gradually over 20 minutes such that the temperature of the contents did not exceed 40° C. Once addition of the sodium hydroxide was completed, the contents were heated, and a reaction was carried out for 10 hours under reflux conditions (99° C.).

The temperature of the reaction liquid was lowered to 60° C. after the reaction had ended. The reaction liquid was left at rest for 10 minutes and then the aqueous phase was removed through a liquid separation operation. The remaining organic phase was analyzed by high-performance liquid chromatography.

As a result, the molar percentages (mol %) of three components (hydroquinone (Ia), monoetherified product (IIIa), and dietherified product (IVa)) contained in the organic phase were determined to be hydroquinone (Ia):monoetherified product (IIIa):dietherified product (IVa)=17.1:77.0:5.9.

(Ia)

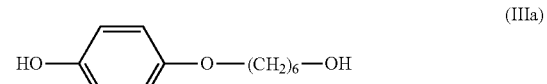

(IIIa)

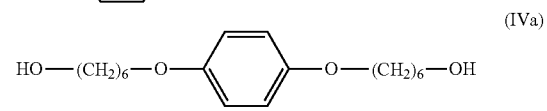

(IVa)

These results indicate that approximately 17 mol % of hydroquinone (Ia) was contained in the organic phase after the reaction and that further purification operation is necessary in order to lower the content of hydroquinone (Ia).

The organic phase obtained after step (1) in a presently disclosed production method is highly susceptible to oxidation, and black discoloration of the solution occurs in a few seconds upon contact with air. Moreover, a state as a homogeneous solution can only be maintained in a heated state of approximately 60° C. because precipitation of crystals occurs upon cooling to approximately 50° C.

The following model solution (1) was prepared as the organic phase after step (1) and was used in an investigation as described below.

Synthesis Example 2 Preparation of Model Solution (1)

A three-necked reaction vessel equipped with a condenser and a thermometer was charged with 104.77 g (0.9515 mol)

of hydroquinone, 100 g (0.7320 mol) of 6-chlorohexanol, 500 g of distilled water, and 100 g of o-xylene in a stream of nitrogen. The entire contents of the reaction vessel were stirred while further adding 35.13 g (0.8784 mol) of sodium hydroxide gradually over 20 minutes such that the temperature of the contents did not exceed 40° C. Once addition of the sodium hydroxide was completed, the contents were heated, and a reaction was carried out for 12 hours under reflux conditions (96° C.)

The temperature of the reaction liquid was lowered to 80° C. after the reaction had ended, and 200 g of distilled water was added. Thereafter, the reaction liquid was cooled to 10° C. to cause precipitation of crystals. Solid-liquid separation was carried out by filtration of the precipitated crystals. The resultant crystals were washed with 500 g of distilled water and were vacuum dried to yield 123.3 g of brown crystals (1).

As a result of analysis of the brown crystals (1) by high-performance liquid chromatography, the molar percentages (mol %) of three components (hydroquinone (Ia), monoetherified product (IIIa), and dietherified product (IVa)) contained in the brown crystals (1) were determined to be hydroquinone (Ia):monoetherified product (IIIa): dietherified product (IVa)=1.3:90.6:8.1.

A homogeneous solution was prepared by adding 5.0 g of the obtained brown crystals (1), 0.524 g (4.76 mmol) of hydroquinone, and 5.0 g of anisole into a sample bottle and heating these materials to 60° C. This solution is referred to as model solution (1).

As a result of analysis of the model solution (1) by high-performance liquid chromatography, the molar percentages (mol %) of three components (hydroquinone (Ia), monoetherified product (IIIa), and dietherified product (IVa)) were determined to be hydroquinone (Ia):monoetherified product (IIIa):dietherified product (IVa)=18.9:74.6: 6.5.

The make-up of the model solution (1) is roughly the same as the liquid make-up of the organic phase obtained after step (1) in Synthesis Example 1.

Examples 1 to 3 and Comparative Examples 1 to 9

A sample bottle of 50 cc in capacity in which a stirrer had been placed was charged with the model solution (1) obtained in Synthesis Example 2, 25.0 g of distilled water, 1.0 g of sodium chloride, and an additive (4.76 mmol) shown below in Table 1. This solution was immersed in a water bath that had been heated to 60° C. and was stirred for 15 minutes. Thereafter, the stirring was stopped, the solution was left at rest for 10 minutes at 60° C. to allow liquid separation, and then the organic phase was collected.

The obtained organic phase (solution composition) was analyzed by high-performance liquid chromatography to calculate the molar percentages (mol %) of hydroquinone (Ia), monoetherified product (IIIa), and dietherified product (IVa) relative to the total of these three components.

The results of analysis are shown below in Table 1.

TABLE 1

| | | Molar percentages of three components in organic phase (mol %) | | |
|---|---|---|---|---|
| | Additive | Hydroquinone | Monoetherified product | Dietherified product |
| Model solution (1) | — | 18.9 | 74.6 | 6.5 |
| Example 1 | Sodium hydroxide | 3.4 | 88.0 | 8.6 |
| Example 2 | Potassium hydroxide | 3.5 | 88.2 | 8.3 |
| Example 3 | Tripotassium phosphate | 3.8 | 87.6 | 8.6 |
| Comparative Example 1 | Sodium carbonate | 6.6 | 84.9 | 8.5 |
| Comparative Example 2 | Sodium hydrogen carbonate | 8.9 | 83.5 | 7.6 |
| Comparative Example 3 | Potassium carbonate | 6.5 | 86.0 | 7.5 |
| Comparative Example 4 | Sodium sulfite | 9.0 | 83.7 | 7.3 |
| Comparative Example 5 | Ammonia | 8.3 | 83.5 | 8.2 |
| Comparative Example 6 | Triethylamine | 8.5 | 84.3 | 7.2 |
| Comparative Example 7 | Pyridine | 10.5 | 82.3 | 7.2 |
| Comparative Example 8 | — | 10.2 | 81.7 | 8.1 |
| Comparative Example 9 | Hydrochloric acid | 10.0 | 81.8 | 8.2 |

The following can be confirmed from Table 1.

The content of hydroquinone (Ia) contained in the organic phase decreased in Examples 1 to 3 in which washing was performed using sodium hydroxide, potassium hydroxide, or tripotassium phosphate as an additive compared to Comparative Examples 1 to 4 in which sodium carbonate, sodium hydrogen carbonate, potassium carbonate, or sodium sulfite was used.

On the other hand, the amount of reduction of hydroquinone (Ia) was small in each of Comparative Examples 5 to 7 in which an amine compound (organic base) was used as an additive and Comparative Examples 8 and 9 in which a neutral or acidic aqueous solution was used as an additive.

Examples 4 to 11

A sample bottle of 50 cc in capacity in which a stirrer had been placed was charged with the model solution (1) obtained in Synthesis Example 2, 25.0 g of distilled water, and 0.300 g (2.38 mmol) of sodium sulfite. Amounts of sodium hydroxide and neutral inorganic salt shown below in Table 2 were added to this solution. Next, the resultant solution was immersed in a water bath that had been heated to 60° C. and the entire contents of the sample bottle were stirred for 15 minutes. Thereafter, the solution was left at rest for 10 minutes at 60° C. to allow liquid separation, and an organic phase and an aqueous phase were obtained. The obtained organic and aqueous phases were analyzed by high-performance liquid chromatography to calculate the molar percentages (mol %) of hydroquinone (Ia), monoetherified product (IIIa), and dietherified product (IVa) relative to the total of these three components.

The results of analysis are shown below in Table 2.

In addition, the amount of sodium hydroxide relative to the number of moles of hydroquinone compound used in excess and the amount of neutral inorganic salt in 1 part by mass of aqueous solution used for washing the organic phase were calculated. These amounts are shown in Table 2. Note that in calculation of the number of moles of hydroquinone compound used in excess, 0.524 g (4.76 mmol) of hydroquinone that was added to compensate for an oxidized portion of hydroquinone in preparation of the model solution (1) was not used. Specifically, the amount of sodium hydroxide relative to the number of moles of hydroquinone compound used in excess was determined by taking the number of moles of hydroquinone compound used in excess to be 0.0089 mol (=[0.9515 mol (amount of hydroquinone charged to three-necked reaction vessel)−0.7320 mol (amount of 6-chlorohexanol charged to three-necked reaction vessel)]×5 g (amount of brown crystals used in preparation of model solution (1))÷123.3 g (amount of brown crystals obtained in three-necked reaction vessel)). Moreover, in calculation of the amount of neutral inorganic salt in 1 part by mass of aqueous solution used for washing the organic phase, the amount of the aqueous solution used for washing the organic phase was taken to be the total amount of distilled water, sodium sulfite, sodium hydroxide, and neutral inorganic salt.

Example 12

A four-necked reaction vessel equipped with a condenser and a thermometer was charged with 104.77 g (0.9515 mol) of hydroquinone, 100 g (0.7320 mol) of 6-chlorohexanol, 4.61 g (0.0366 mol) of sodium sulfite, 300 g of distilled water, and 100 g of anisole in a stream of nitrogen. The entire contents were heated under stirring and 117.11 g (0.8784 mol) of 30 mass % sodium hydroxide aqueous solution was added dropwise over 5 hours under reflux conditions (99° C.). A reaction was then carried out for a further 10 hours under reflux conditions.

The temperature of the reaction liquid was lowered to 60° C. after the reaction had ended and stirring of the reaction liquid was stopped. The reaction liquid was left at rest for 15 minutes at 60° C. to allow liquid separation, and then the aqueous phase was removed. Next, 4.61 g (0.0366 mol) of sodium sulfite, 450 g of distilled water, 17.57 g (0.1318 mol) of 30 mass % sodium hydroxide aqueous solution, and 75 g of sodium sulfate were added to the resultant organic phase

TABLE 2

| | Sodium hydroxide | | Neutral inorganic salt | | | Molar percentages of three components in organic phase (mol %) | | | Molar percentages of three components in aqueous phase (mol %) | | |
| --- | --- | --- | --- | --- | --- | --- | --- | --- | --- | --- | --- |
| | Additive amount (g) | Amount relative to number of moles of hydroquinone compound used in excess (molar equivalents) | Type | Additive amount (g) | Amount in 1 part by mass of aqueous solution used for washing organic phase (parts by mass) | Hydroquinone | Monoetherified product | Dietherified product | Hydroquinone | Monoetherified product | Dietherified product |
| Example 4 | 0.190 | 0.533 | Sodium chloride | 1.000 | 0.038 | 3.8 | 87.2 | 9.0 | 65.7 | 34.3 | 0.0 |
| Example 5 | 0.190 | 0.533 | Sodium chloride | 3.000 | 0.105 | 3.2 | 88.6 | 8.2 | 83.9 | 16.1 | 0.0 |
| Example 6 | 0.238 | 0.668 | Sodium chloride | 3.000 | 0.105 | 1.9 | 89.7 | 8.4 | 79.8 | 20.2 | 0.0 |
| Example 7 | 0.285 | 0.800 | Sodium chloride | 3.000 | 0.105 | 1.1 | 90.0 | 8.9 | 72.8 | 27.2 | 0.0 |
| Example 8 | 0.285 | 0.800 | Sodium chloride | 4.000 | 0.135 | 0.8 | 90.3 | 8.9 | 77.0 | 23.0 | 0.0 |
| Example 9 | 0.285 | 0.800 | Sodium chloride | 6.000 | 0.190 | 0.7 | 89.9 | 9.4 | 83.9 | 16.1 | 0.0 |
| Example 10 | 0.285 | 0.800 | Sodium chloride | 8.000 | 0.238 | 1.2 | 89.4 | 9.4 | 89.6 | 10.4 | 0.0 |
| Example 11 | 0.285 | 0.800 | Sodium sulfate | 6.000 | 0.190 | 0.7 | 90.8 | 8.5 | 87.2 | 12.8 | 0.0 |

Table 2 shows that by optimizing the amount of sodium hydroxide (amount of alkali) and the amount of neutral inorganic salt that are used, it is possible to cause hydroquinone to move into the aqueous phase with higher selectivity and to increase the proportion of the target monoetherified product in the organic phase.

Specifically, it can be seen that it is important to adjust the amount of alkali in accordance with the amount of hydroquinone (Ia) that is contained and also to adjust solubility in the aqueous solution through the amount of neutral inorganic salt in order to obtain an ideal equilibrium state of four components (hydroquinone (Ia), alkali salt of hydroquinone (Ia), monoetherified product (IIIa), and alkali salt of monoetherified product (IIIa)) between the organic phase and the aqueous phase.

Moreover, Example 11 demonstrates that the neutral inorganic salt used in this operation is not limited to sodium chloride and may alternatively be a sulfate, a representative example of which is sodium sulfate.

and the entire contents were stirred for 30 minutes at 60° C. The contents were then left at rest for 15 minutes to allow liquid separation, and the aqueous phase was removed.

As a result of analysis of the resultant organic phase (solution composition) by high-performance liquid chromatography, the molar percentages (mol %) of three components (hydroquinone (Ia), monoetherified product (IIIa), and dietherified product (IVa)) were determined to be hydroquinone (Ia):monoetherified product (IIIa):dietherified product (IVa)=1.4:92.7:5.9.

Next, 1.61 g (0.0073 mol) of 2,6-di(t-butyl)-4-methylphenol (BHT) and 50 g of toluene were added to the solution composition, a Dean-Stark apparatus was attached to the reaction vessel, and piping from a vacuum pump was set-up at an upper part of the condenser. Pressure reduction was started with the solution in a heated and stirred state, and the system was dehydrated by removing water through the Dean-Stark apparatus while adjusting the degree of vacuum (reaction vessel internal pressure: 10 kPa to 30 kPa) such that reflux conditions were reached at a solution temperature of 60° C. to 65° C.

Thereafter, the inside of the reaction vessel was returned to normal pressure with nitrogen, 145.05 g (2.0129 mol) of acrylic acid and 17.59 g (0.1830 mol) of methanesulfonic acid were added in order, and then pressure reduction was started again. Produced water was removed and a dehydration reaction was carried out while adjusting the degree of vacuum (reaction vessel internal pressure: 8 kPa to 10 kPa) such that reflux conditions were reached at a reaction liquid temperature of 60° C. to 65° C. The reaction was continued for 4 hours after addition of the methanesulfonic acid.

Next, the reaction liquid was cooled to 40° C., 100 g of distilled water was added, and 435.00 g (0.7869 mol) of 25 mass % potassium carbonate aqueous solution was added dropwise over 30 minutes. Thereafter, 50 g of sodium chloride and 50 g of n-hexane were further added, stirring was performed for 30 minutes at 40° C., and then the organic phase was collected by liquid separation. After adding 500 g of distilled water and 150 g of sodium chloride to the resultant organic phase, liquid separation was performed at 40° C. to collect the organic phase. Moreover, after adding 400 g of distilled water and 40 g of sodium chloride to the resultant organic phase, liquid separation was performed at 40° C. to collect the organic phase. Next, 3.0 g of an adsorbent (produced by Kyowa Chemical Industry Co., Ltd.; product name: KYOWAAD 700SEN-S) was added to the obtained organic phase, and the entire contents were stirred for 30 minutes at 25° C. and were then filtered.

Next, 0.81 g (0.0037 mol) of BHT was added to the resultant filtrate to obtain a solution that was subsequently cooled to 15° C. Crystals were precipitated by adding 0.02 g of seed crystals to the cooled solution and adding 350 g of n-hexane dropwise over 1.5 hours. Thereafter, the solution was cooled to 10° C., 0.6 g of an antistatic agent (produced by Innospec Inc.; product name: STADIS-450) was added to the solution, and the crystals were collected by filtration. The obtained crystals were washed with a mixed liquid of 66.7 g of toluene, 133.3 g of n-heptane, 0.2 g of an antistatic agent (produced by Innospec Inc.; product name: STADIS-450) and were vacuum dried to yield 119.8 g of 6-[(4-hydroxyphenyl)oxy]hexyl acrylate as a white solid (yield based on 6-chlorohexanol: 62%; purity: 95.7%).

The structure of the target was identified by $^1$H-NMR. The results are shown below.

$^1$H-NMR (500 MHz, DMSO-d$_6$, TMS, δ ppm): 8.87 (s, 1H), 6.72 (d, 2H, J=9.0 Hz), 6.65 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.83 (t, 2H, J=6.5 Hz), 1.56-1.72 (m, 4H), 1.31-1.47 (m, 4H)

Example 13

Operations were carried out in the same way as in Example 12 with the exception that sodium sulfate used for washing the organic phase with an aqueous solution in Example 12 was changed to sodium chloride.

As a result of analysis of the solution composition of the resultant organic phase by high-performance liquid chromatography, the molar percentages (mol %) of three components (hydroquinone (Ia), monoetherified product (IIIa), and dietherified product (IVa)) were determined to be hydroquinone (Ia):monoetherified product (IIIa):dietherified product (IVa)=1.7:92.0:6.3.

An esterification reaction with acrylic acid and purification operations were implemented in the same way as in Example 12 using the obtained solution composition to yield 116.5 g of 6-[(4-hydroxyphenyl)oxy]hexyl acrylate as a white solid (yield based on 6-chlorohexanol: 60%; purity: 94.5%).

As a result of analysis of the obtained white solid by high-performance liquid chromatography, the peak area of a component present in greatest quantity as an impurity (component having a largest peak area among impurities) was determined to be 0.6 area %. The white solid was purified by silica gel column chromatography (developing solvent: toluene:ethyl acetate=9:1 [volume ratio]) and using a preparative GPC apparatus (produced by Japan Analytical Industry Co., Ltd.; product name: LC908-C60) to isolate the component present in greatest quantity as an impurity.

As a result of structural identification by $^1$H-NMR, the component present in greatest quantity as an impurity was determined to be a compound of the following formula (VIIa) (hereinafter, referred to as "compound (VIIa)"). The results of $^1$H-NMR are shown below.

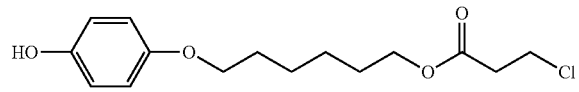

(VIIa)

$^1$H-NMR (500 MHz, CDCl$_3$, TMS, δ ppm): 6.78 (d, 2H, J=9.0 Hz), 6.76 (d, 2H, J=9.0 Hz), 4.91 (s, 1H), 4.14 (t, 2H, J=6.5 Hz), 3.89 (t, 2H, J=6.5 Hz), 3.76 (t, 2H, J=6.5 Hz), 2.79 (t, 2H, J=6.5 Hz), 1.65-1.79 (m, 4H), 1.41-1.50 (m, 4H)

The presence of compound (VIIa) was not confirmed in Example 12.

Examples 12 and 13 differ only in terms that "sodium sulfate" and "sodium chloride" were respectively used therein as the neutral inorganic salt. Therefore, it is presumed that a portion of the sodium chloride-containing aqueous solution used for washing the organic phase in Example 13 became mixed into the esterification reaction, the sodium chloride reacted with methanesulfonic acid used as an acid catalyst for the esterification reaction to produce hydrochloric acid, and this hydrochloric acid added at acrylic groups to cause production of the compound (VIIa).

Depending on the application for which the polymerizable compound is to be used, the presence of the compound (VIIa) may be problematic. Examples 12 and 13 demonstrate that in such a situation, it is preferable to use a sulfate such as sodium sulfate that does not include a halogen as the neutral inorganic salt.

The invention claimed is:
1. A method of producing a solution composition containing a monoetherified product, comprising:
   a step (1) of reacting a hydroquinone compound of formula (I), shown below,

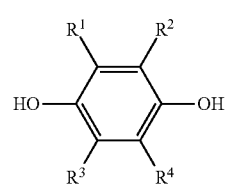

(I)

where $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6, and a hydroxyl group-containing etherifying agent of formula (II), shown below,

HO—R⁵—X  (II)

where R⁵ represents an optionally substituted alkylene group having a carbon number of 1 to 20 and X represents a leaving group, in a two-phase system including an alkaline aqueous solution and a hydrophobic ether solvent, and in the absence of a phase transfer catalyst and a hydrophilic organic solvent; and a step (2a) of, after the step (1), separating and removing an aqueous phase of a two-phase reaction liquid by liquid separation, and washing an organic phase using an aqueous solution containing a neutral inorganic salt and a hydroxide of an alkali metal or alkaline earth metal or a phosphate of an alkali metal or alkaline earth metal, wherein the monoetherified product is a monoetherified product of formula (III), shown below,

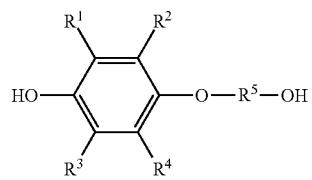
(III)

where R¹ to R⁵ represent the same as above.

2. The method of producing a solution composition according to claim 1, wherein
the hydroxide of an alkali metal or alkaline earth metal is sodium hydroxide or potassium hydroxide.

3. A method of producing a solution composition comprising:

a step (1) of reacting a hydroquinone compound of formula (I), shown below,

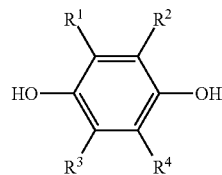
(I)

where R¹, R², R³, and R⁴ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6, and a hydroxyl group-containing etherifying agent of formula (II), shown below,

HO—R⁵—X  (II)

where R⁵ represents an optionally substituted alkylene group having a carbon number of 1 to 20 and X represents a leaving group, in a two-phase system including an alkaline aqueous solution and a hydrophobic ether solvent, and in the absence of a phase transfer catalyst and a hydrophilic organic solvent; and a step (2b) of, after the step (1), separating and removing an aqueous phase of a two-phase reaction liquid by liquid separation, and washing an organic phase using an aqueous solution containing an alkali and a neutral inorganic salt, wherein the solution composition contains: the hydroquinone compound; a monoetherified product of formula (III), shown below,

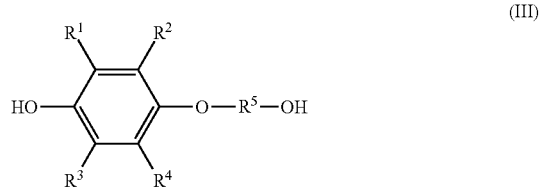
(III)

where R¹ to R⁵ represent the same as above; and a dietherified product of formula (IV), shown below,

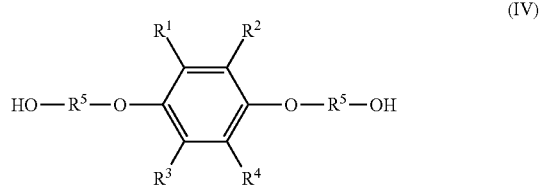
(IV)

where R¹ to R⁵ represent the same as above, and the hydroquinone compound has a molar percentage of 5.0 mol % or less, the monoetherified product has a molar percentage of 85 mol % or more, and the dietherified product has a molar percentage of 10.0 mol % or less relative to the total of the hydroquinone compound, the monoetherified product, and the dietherified product.

4. The method of producing a solution composition according to claim 1, wherein
the hydrophobic ether solvent is anisole or cyclopentyl methyl ether.

5. The method of producing a solution composition according to claim 1, wherein
the neutral inorganic salt is sodium chloride or a sulfate.

6. The method of producing a solution composition according to claim 1, wherein
the neutral inorganic salt is sodium sulfate.

7. A solution composition comprising:
a hydroquinone compound of formula (I), shown below,

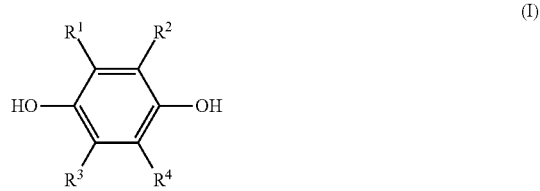
(I)

where R¹, R², R³, and R⁴ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6;

a monoetherified product of formula (III), shown below,

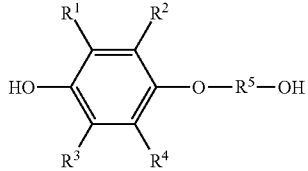
(III)

where $R^1$ to $R^4$ represent the same as above and $R^5$ represents an optionally substituted alkylene group having a carbon number of 1 to 20;

a dietherified product of formula (IV), shown below,

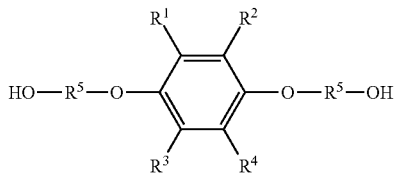
(IV)

where $R^1$ to $R^5$ represent the same as above; and a hydrophobic ether solvent, wherein the hydroquinone compound has a molar percentage of 5.0 mol % or less, the monoetherified product has a molar percentage of 85 mol % or more, and the dietherified product has a molar percentage of 10.0 mol % or less relative to the total of the hydroquinone compound, the monoetherified product, and the dietherified product.

8. The solution composition according to claim 7, wherein the hydrophobic ether solvent is anisole or cyclopentyl methyl ether.

9. A method of producing a polymerizable compound comprising a step (3) of adding an acid catalyst and a carboxylic acid compound of formula (V), shown below,

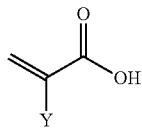
(V)

where Y represents a hydrogen atom, a methyl group, or a chlorine atom, to a solution composition that is the solution composition according to claim 7, and reacting the carboxylic acid compound with the monoetherified product contained in the solution composition, wherein the polymerizable compound is a polymerizable compound of formula (VI), shown below,

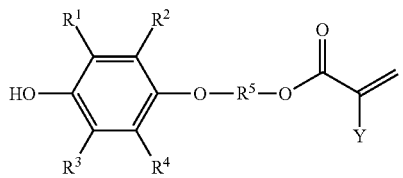
(VI)

where $R^1$ to $R^5$ and Y represent the same as above.

10. The method of producing a polymerizable compound according to claim 9, further comprising a step of producing the solution composition, comprising:

a step (1) of reacting a hydroquinone compound of formula (I), shown below,

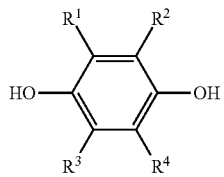
(I)

where $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6, and a hydroxyl group-containing etherifying agent of formula (II), shown below,

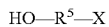
HO—$R^5$—X (II)

where $R^5$ represents an optionally substituted alkylene group having a carbon number of 1 to 20 and X represents a leaving group, in a two-phase system including an alkaline aqueous solution and a hydrophobic ether solvent, and in the absence of a phase transfer catalyst and a hydrophilic organic solvent; and a step (2a) of, after the step (1), separating and removing an aqueous phase of a two-phase reaction liquid by liquid separation, and washing an organic phase using an aqueous solution containing a sodium sulfate and a hydroxide of an alkali metal or alkaline earth metal or a phosphate of an alkali metal or alkaline earth metal, wherein the monoetherified product is a monoetherified product of formula (III), shown below,

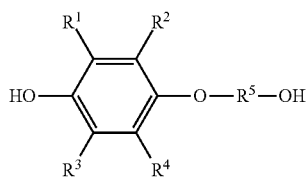
(III)

where $R^1$ to $R^5$ represent the same as above.

11. The method of producing a polymerizable compound according to claim 9, wherein the carboxylic acid compound is acrylic acid.

12. The method of producing a solution composition according to claim 3, wherein the hydrophobic ether solvent is anisole or cyclopentyl methyl ether.

13. The method of producing a solution composition according to claim 3, wherein
the neutral inorganic salt is sodium chloride or a sulfate.

14. The method of producing a solution composition according to claim 3, wherein
the neutral inorganic salt is sodium sulfate.

15. The method of producing a polymerizable compound according to claim 9, further comprising
a step of producing the solution composition, comprising:
a step (1) of reacting a hydroquinone compound of formula (I), shown below,

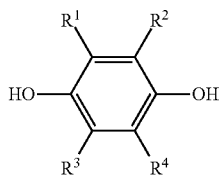

(I)

where $R^1$, $R^2$, $R^3$, and $R^4$ each represent, independently of one another, a hydrogen atom, a halogen atom, an optionally substituted alkyl group having a carbon number of 1 to 6, a —C(=O)—O—R' group, or a —C(=O)—R' group, with R' representing an optionally substituted alkyl group having a carbon number of 1 to 6, and a hydroxyl group-containing etherifying agent of formula (II), shown below,

HO—$R^5$—X   (II)

where $R^5$ represents an optionally substituted alkylene group having a carbon number of 1 to 20 and X represents a leaving group, in a two-phase system including an alkaline aqueous solution and a hydrophobic ether solvent, and in the absence of a phase transfer catalyst and a hydrophilic organic solvent; and a step (2b) of, after the step (1), separating and removing an aqueous phase of a two-phase reaction liquid by liquid separation, and washing an organic phase using an aqueous solution containing an alkali and a sodium sulfate, wherein
the solution composition contains: the hydroquinone compound; a monoetherified product of formula (III), shown below,

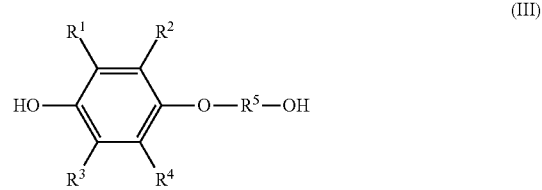

(III)

where $R^1$ to $R^5$ represent the same as above; and a dietherified product of formula (IV), shown below,

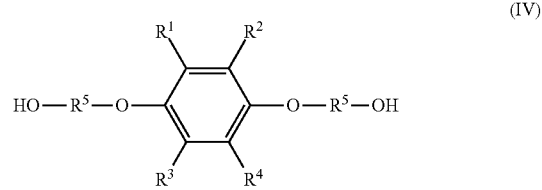

(IV)

where $R^1$ to $R^5$ represent the same as above, and the hydroquinone compound has a molar percentage of 5.0 mol % or less, the monoetherified product has a molar percentage of 85 mol % or more, and the dietherified product has a molar percentage of 10.0 mol % or less relative to the total of the hydroquinone compound, the monoetherified product, and the dietherified product.

* * * * *